United States Patent
Malmgren et al.

(10) Patent No.: US 6,544,534 B2
(45) Date of Patent: Apr. 8, 2003

(54) CONDITIONER THAT PROVIDES SKIN LIKE AN ANGEL

(76) Inventors: Janice K. Malmgren, 8815 Woodbrook Dr., Dallas, TX (US) 75243; Sonya K. Moreno, 304 Wedgewood Ln., Cedar Hill, TX (US) 75104

( * ) Notice: Subject to any disclaimer, the term of this patent is extended or adjusted under 35 U.S.C. 154(b) by 0 days.

(21) Appl. No.: 09/934,351

(22) Filed: Aug. 21, 2001

(65) Prior Publication Data

US 2003/0039625 A1 Feb. 27, 2003

(51) Int. Cl.[7] ............... A61K 6/00; A61K 7/00; A61K 7/06; A61K 31/74
(52) U.S. Cl. ............ 424/401; 424/400; 424/70.1; 424/74; 424/78.02; 424/725
(58) Field of Search .............. 424/401, 70.1, 424/73, 74, 78.03, 744, 735

(56) References Cited

U.S. PATENT DOCUMENTS 4,784,849 A * 11/1988 Tutsky ............... 424/73
5,866,145 A * 2/1999 Stavroff et al. ............ 424/401

* cited by examiner

Primary Examiner—Michael G. Hartley
Assistant Examiner—Sharmila S. Gollamudi
(74) Attorney, Agent, or Firm—Seto Patents; Jeffrey K. Seto

(57) ABSTRACT

A skin conditioner made of all natural ingredients that eliminates body dandruff leaving the skin able to breathe and feeling soft and supple; "skin like an angel". The conditioner can be heated prior to application in order to provide a more relaxing feel to the user and is massaged into the skin of all or part of the body. Thereafter, the conditioner is rinsed or showered off. The conditioner can also be massaged into the scalp to eliminate dandruff and condition the scalp and hair. Ingredients of the conditioner include sea salt, Epsom salt, almond oil, apricot kernel oil, avocado oil, jojoba oil, aloe vera gel, castor oil, vitamin E, vegetable glycerin and soap. Essential oils may optionally be included in the conditioner to add fragrance. The preferred soap is castile however other soaps such as antibacterial soap can be used. If the product is heated prior to use, it should not be heated above 100° F. in order to prevent a change in the molecular structure of some of the ingredients.

14 Claims, 5 Drawing Sheets

CONDITIONER THAT PROVIDES SKIN LIKE AN ANGEL

BACKGROUND OF THE INVENTION

The present invention relates generally to skin conditioners and more particularly to a skin conditioner made of all natural ingredients that eliminates body dandruff and provides the user with skin like an angel.

The skin is the largest organ in the human body. It is a protective organ covering the external surface of the body. The skin forms a protective barrier against the action of physical, chemical, and bacterial agents on the deeper tissues and contains the special sensitive end organs for the sense of touch. Through the activity of its sweat glands and blood vessels, it also plays an important role in maintaining body temperature. One square inch of skin contains up to 15 feet of blood vessels, which have as one of their functions the regulation of body temperature. Each square inch of skin also contains hundreds of sweat glands that are controlled by a heat regulation center in the brain. These glands secrete moisture, which evaporates, cools the body surface, and helps maintain normal body temperature. In this capacity the skin acts as an excretory organ. The skin is elastic, and except for a few areas such as the palms, soles, and ears, is loosely attached to the underlying tissues. The skin varies in thickness from 0.02 inches (in.) on the eyelids to 0.17 in. or more on the palms and soles.

In structure the skin is composed of two distinct layers. The outer layer, called the epidermis is several cells thick and has an external, horny layer of dead cells that are constantly shedding from the surface. The dead cells, sometimes referred to as body dandruff, are replaced by new cells from a lower basal layer of cells called the stratum germinativum. The inner layer, called the dermis, is composed of a network of collagen and elastic fibers, blood vessels, nerves, fat lobules, and the bases of hair follicles and sweat glands.

Sweat glands are found on every part of the body. They are numerous on the palms and soles but relatively sparse on the skin of the back. Each gland consists of coiled tubules that are situated in the subcutaneous tissue and a duct that extends through the dermis and forms a convoluted spiral through the epidermis. Sebaceous glands, saclike glands that secrete the sebum that lubricates and softens the skin, open into the hair follicles a short distance below the surface of the epidermis.

In order to maintain the elasticity of the skin and supplement the work done by the sebaceous glands many people regularly apply man made conditioners to their skin. Maintaining the proper functioning of the skin is important in regards to preventing pre-mature aging and regulating body temperature. One way to help the skin properly function is to aid in the removal of dead skin cells. Removal of dead skin cells not only prevents blockage of sweat and sebaceous glands but also promotes the production of healthy new skin cells. The present invention uses only natural ingredients to promote the growth of healthy new skin cells and maintain the proper functioning of the skin.

Salt, also known as sodium chloride, is a chemical compound that has the formula NaCl. Salts are characterized by ionic bonds, relatively high melting points, and a crystalline structure when in the solid state. Salt is widely distributed in nature. It is found in solution in ocean water in concentrations of about 4.08 oz./gallon of water and is the source of sea salt. Epsom salt is the common name for a colorless or white crystalline salt, magnesium sulfate hepta-hydrate, $MgSO_4 \cdot 7H_2O$, found in the minerals kieserite and epsomite and in mineral waters. Epsom salt was first prepared at Epsom, England. The salt has a bitter taste. It is used in medicine as a cathartic and in hypertonic baths to reduce swelling.

Almond is the common name for a small tree of the rose family and for the kernel of its fruit. The tree is characterized by the coarsely furrowed and wrinkled shell of the drupe and by the young leaves that have their sides folded along the central vein. The almond tree grows up to 30 ft. high and is native to western Asia and southern Europe and is cultivated in the United States. The almond is valued chiefly for its nut, which is an important article of commerce. Varieties are classified as either sweet or bitter. Sweet almonds contain a large quantity of a bland, fixed oil. Sweet almonds have an agreeable taste and are nutritious. The long almonds of Málaga, Spain, known as Jordan almonds, and the broad almonds of Valencia, Spain, are the most valued.

Apricot is the common name for a tree of the rose family native to eastern Asia, and for its fruit. The tree is small, with heart-shaped leaves on long stalks. The fruit, which resembles the peach, is roundish, downy, yellow, and sometimes ruddy on one side, with yellow flesh. More than 20 kinds of apricots are distinguished. The fruit, somewhat smaller than a peach, is known for its delicate flavor. It is marketed fresh, as well as dried and packed. Large quantities are canned or pulped for jam making. California and Oregon are the leading producers in the United States.

Avocado, also known as alligator pear, is the common name for a tree native to tropical America, and for the fruit of this tree. The fruit is a greenish, thick-skinned drupe, similar in size and shape to a large pear. When ripe, the flesh has the consistency of firm butter and a faint nutlike flavor. It has a high fat content, containing 10 to 20 percent oil, and is rich in protein. In the United States avocado is popular as a salad vegetable, and in the tropics it is often used in soup. The tree is extensively cultivated in the southern United States and California.

Jojoba is the common name for the plant family Spurge, and for its only member, a shrub that is under development as a crop for semiarid lands. Found in the United States-Mexican Sonoran Desert, the jojoba is valued for the oil derived from its seeds, which are about 50 percent oil by weight. At present the oil is mainly used for lotions, shampoos, and conditioners, but it has potential for lubricants and other applications, including substitution for vegetable oil in food and, in hydrogenated form, for waxes and candles. The plant grows to about 20 ft. high and takes about 10 years to develop fully. Plantations that grow jojoba now exist in Arizona, California, Mexico, several Mideastern nations, Ghana, and Australia.

Aloe is the common name and genus of plants with more than 150 species, most native to South Africa. They usually have short stems, fleshy, lanceolate leaves crowded in rosettes at the end of the stem, and red or yellow tubular flowers in dense clusters. Species vary in height from several inches to more than 30 ft. They are widely cultivated as garden and tub plants. Several species are commercially important as the source of the aloes used in medicine.

Castor oil is colorless or yellow to yellowish-brown and thick, oily liquid is obtained from the seeds of the castor-oil plant. Although it has a disagreeable taste, it is practically odorless. It is insoluble in water, but soluble in organic solvents. The medicinal oil is prepared from husked seeds. Unhusked seeds, the source of industrial castor oil, yield from 45 to 55 percent oil. The oil is pressed from the seeds and can be purified and bleached. In addition to its use as a simple purgative, castor oil is used as a plasticizer in nitrocellulose compositions, in cosmetics, and in insulation products.

Vitamin E was first isolated in a pure form in 1933 by Gladys Emerson, an American biochemist and nutritionist. Vitamin E is an essential nutrient for many vertebrate animals. It has been popularly advocated for a great variety of afflictions, but its exact role in the human body is still under research. Vitamin E is found in seed oils and wheat germ.

Glycerol or Glycerin, is a colorless, odorless, sweet-tasting alcohol, $C_3H_8O_3$, with a specific gravity of 1.26. It forms a solution with water in any proportion, and dissolves in alcohol in all proportions, but is insoluble in ether and many other organic solvents. The term glycerol refers specifically to the compound, the formula of which is given above, whereas glycerin may also refer to glycerite (glycerol in solution) or other solutions of or preparations made from glycerol. Simple fats and oils are esters of fatty acids and glycerol. Obtained as a by-product of soap manufacture, after fats and oils have been treated with alkali to form the soap, crude glycerol is purified by distillation. Of the annual glycerol production in the U.S. about 40 percent comes from soap making. The most common use for glycerol is in the making of plastics. Other important applications are in the preparation of drugs and toilet articles, including toothpastes and as a plasticizer in cellophane.

Vegetables are the edible product of herbaceous plants; plants with a soft stem. Vegetables can be grouped according to the edible part of each plant: leaves (lettuce), stalks (celery), roots (carrot), tubers (potato), bulbs (onion), and flowers (broccoli). In addition, fruits such as the tomato and seeds such as the pea are commonly considered vegetables. Most vegetables are valuable sources of vitamins, minerals, and fiber and are low in fat and calories.

Soaps, also known as cleansing agents or detergents, are made from animal and vegetable fats, oils, and greases. Chemically, the sodium or potassium salt of a fatty acid, is formed by the interaction of fats and oils with alkali. Oils and fats used are compounds of glycerin and a fatty acid, such as palmitic, or stearic acid. When these compounds are treated with an aqueous solution of an alkali, such as sodium hydroxide, in a process called saponification, they decompose, forming glycerin and the sodium salt of the fatty acid. The fat palmitin, for example, which is the ester of glycerin and palmitic acid, yields sodium palmitate (soap) and glycerin upon saponification. The fatty acids required for soap making are supplied by tallow, grease, fish oils, and vegetable oils such as coconut oil, olive oil, palm oil, soybean oil, and corn oil. Hard soaps are made from oils and fats that contain a high percentage of saturated acids, which are saponified with sodium hydroxide. Soft soaps are semi-fluid soaps made from linseed oil, cotton-seed oil, and fish oils, which are saponified with potassium hydroxide. A fine toilet soap made of high-grade olive oil is known as castile soap.

Pressing is a well known technique for extracting oil from seeds, nuts and other plant products. The modern screw press is the successor to the hydraulic press and provides continuous processing, greater capacity, requires less labor, and generally removes more oil. As ground seed is fed continuously into the mechanical press, a worm screw increases the pressure progressively as the material moves though a slotted barrel. Pressures from 10,000 to 30,000 pound per square inch are attainable. The oil is squeezed out though the slots, leaving a cake with only 3 to 5 percent of the original amount of oil. A general sequence of modern operation in pressing seeds and nuts includes: passing seeds over a magnetic separator to remove any stray bits of metal; removing shells or hulls; converting kernels or meats into coarse meal by grinding them between grooved rollers or with special types of hammer mills; and, pressing in hydraulic or screw presses with or without preliminary heating, depending on the type of oil-bearing material and the quality of oil desired. Oil expressed without heating contains the least amount of impurities and is often of edible quality without refining or further processing. Such oils are known as cold pressed, cold drawn or virgin oils.

The present conditioner take advantage of the benefits provided by cold pressed oils and other natural substances.

SUMMARY OF THE INVENTION

A skin conditioner is provided that is massaged into the skin and thereafter rinsed or showered off. The skin conditioner contains all natural ingredients and provides users with the benefits of eliminating body dandruff, leaving the skin able to breathe, and feeling soft and supple, herein referred to as "skin like and angel". The conditioner is made of sea salt, Epsom salt, almond oil, apricot kernel oil, avocado oil, jojoba oil, aloe vera gel, castor oil, vitamin E, vegetable glycerin and soap. The proportion of sea salt to Epsom salt is 2 to 1. A first group of natural ingredients comprising cold expeller pressed oils of almond, apricot kernel, avocado and jojoba, along with aloe vera gel, these ingredients are provided in near equal amounts. The second group of natural ingredients comprising castor oil, vitamin E, vegetable glycerin and soap are provided in amounts substantially smaller than the amounts of the first group.

The skin conditioner can be applied by hand or through the use of an applicator and may be applied to the skin of the entire body. The skin conditioner can even be applied to the scalp to eliminate dandruff and condition the scalp and hair. The conditioner can optionally be heated prior to application. The warmed conditioner provides therapeutic benefits by relaxing and soothing the user during application. Essential oils can also optionally be added to provide a pleasant fragrance to the conditioner.

BRIEF DESCRIPTION OF THE DRAWINGS

The invention of the present application will now be described in more detail with reference to the accompanying drawings, given only by way of example, in which.

DETAILED DESCRIPTION OF THE INVENTION

Figure 1:
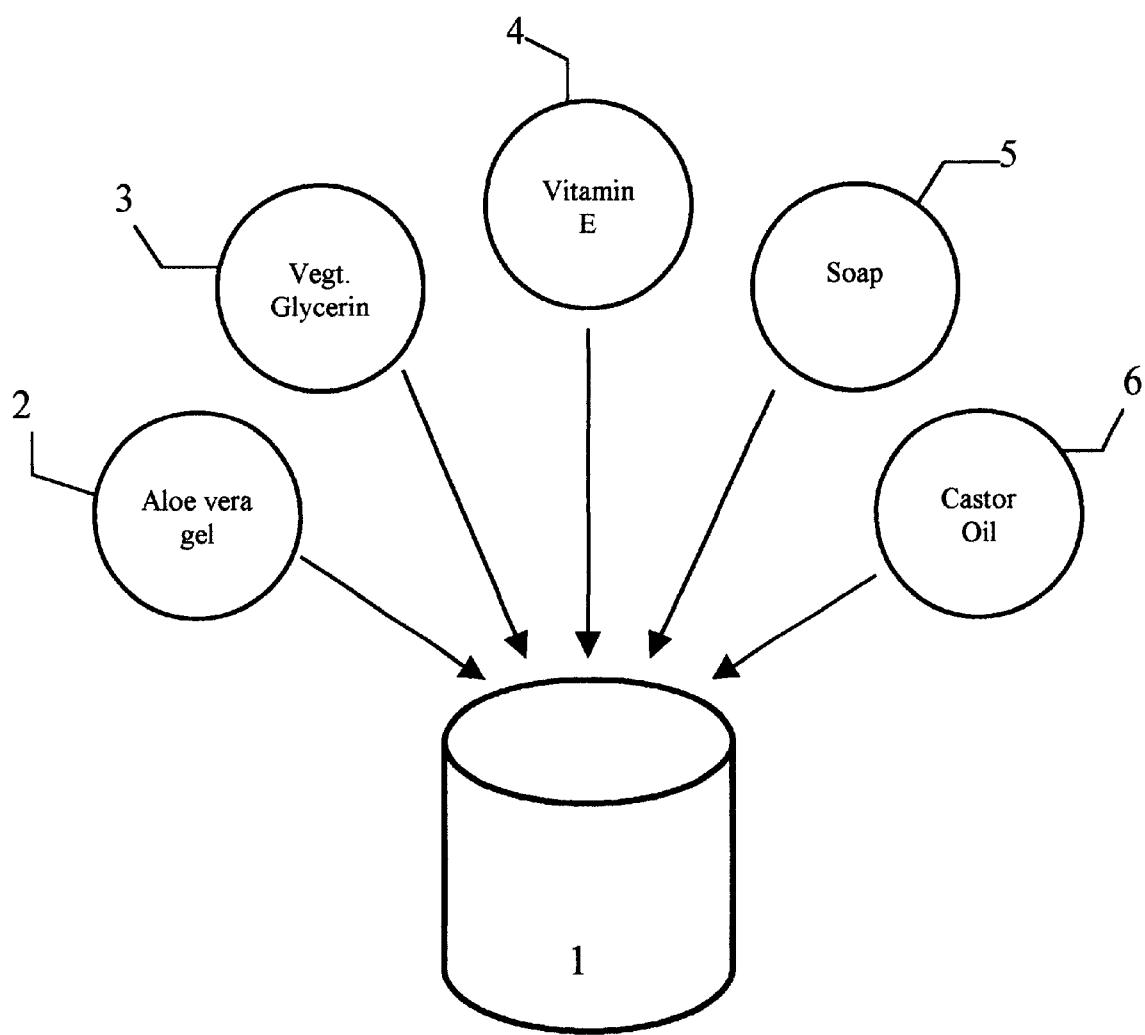
FIG. 1 illustrates the first stage of making the present conditioner.

Referring to FIG. 1, empty mixing container 1 is provided to receive all of the ingredients for the present conditioner. In the first stage of producing the conditioner five ingredients are added to mixing container 1. These first five ingredients are aloe vera gel 2, vegetable glycerin 3, vitamin E 4, soap 5, and castor oil 6. Preferably, castile soap is used however other types of soap such as antibacterial soap may also be used. The amount of each ingredient depends on the total amount of conditioner to be made. In this example, the amount of each ingredient will be given so that approximately one half of a gallon of conditioner is produced. Of course each amount can be proportionately increased or decreased so that larger or smaller batches can be made. The required amounts of the first five ingredients for a half gallon batch are: one cup of aloe vera gel 2; one tablespoon of vegetable glycerin 3; one teaspoon of vitamin E 4; one tablespoon of soap 5; and, one tablespoon of castor oil 6. These ingredients are placed into mixing container 1 and beaten together thoroughly.

Figure 2:
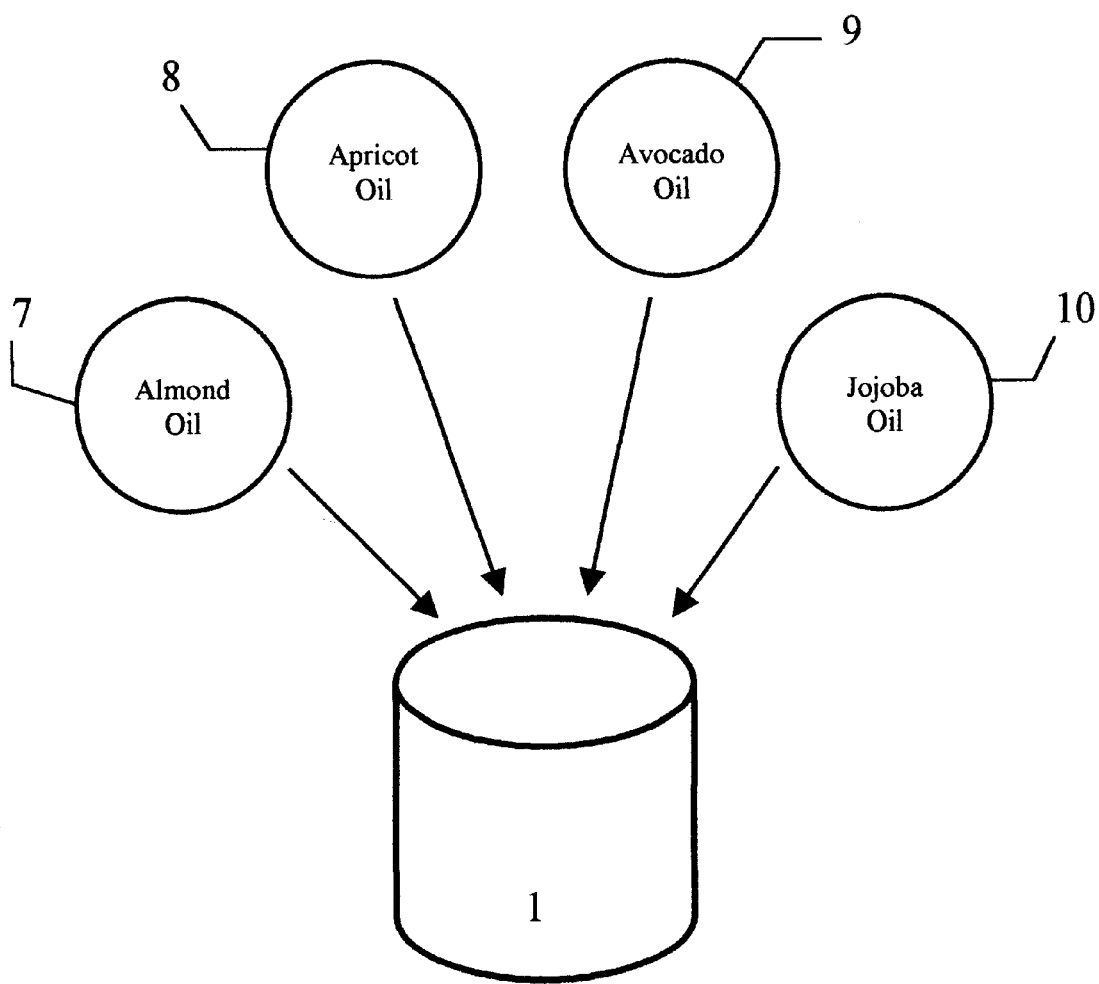
FIG. 2 illustrates the second stage of making the present conditioner.

Production of the present conditioner continues with reference to FIG. 2, which shows the four ingredients that are added to container 1 in the second stage of production. This second group of ingredients include cold pressed almond oil 7, apricot kernel oil 8, avocado oil 9, and jojoba oil 10. Three quarters of a cup of each of these four ingredients are added to container 1 and mixed thoroughly with the ingredients of stage one. The amounts of almond oil 7, apricot kernel oil 8, avocado oil 9, and jojoba oil 10 provided above are also associated with making a batch of approximately half a gallon. As mentioned above, other proportional quantities can be used to make smaller and larger batches.

Figure 3:
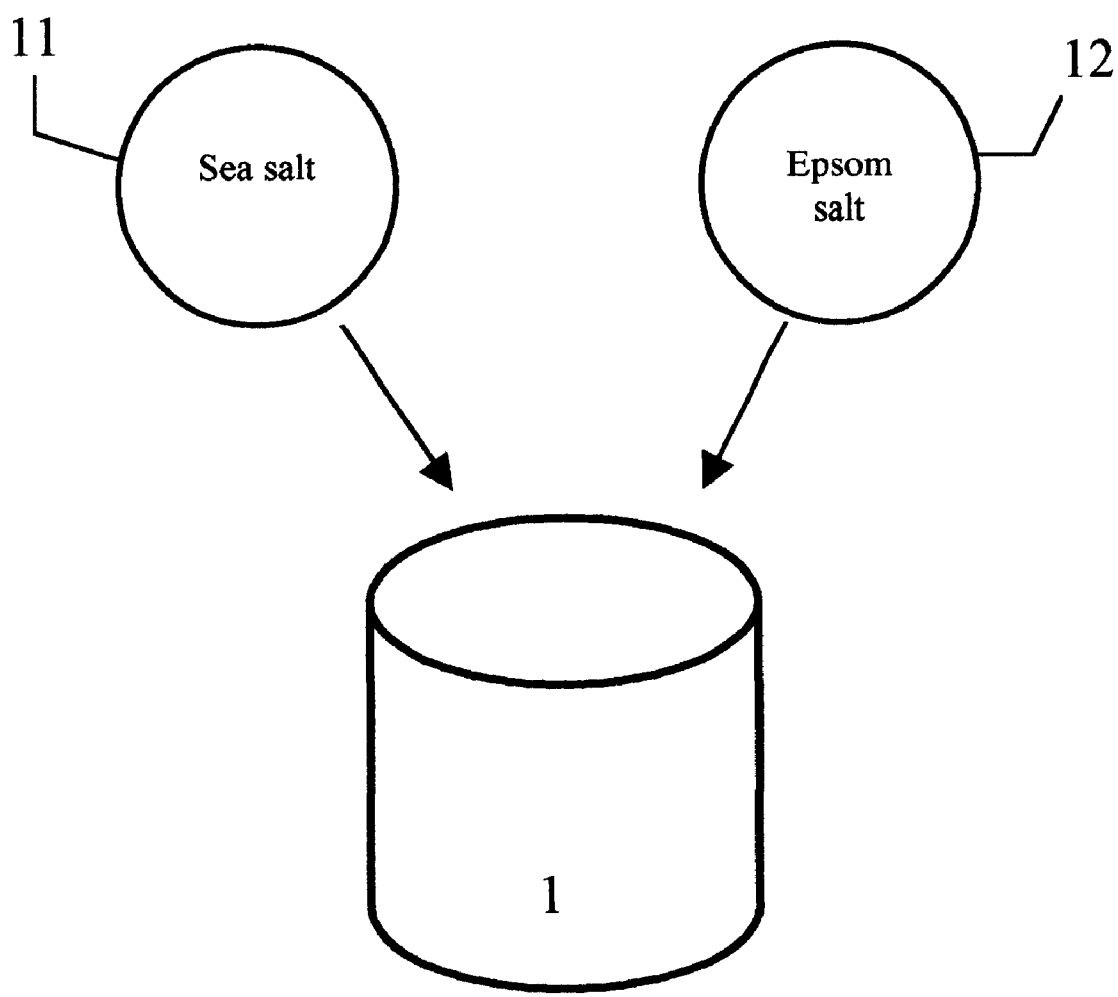
FIG. 3 illustrates the third stage of making the present conditioner.

FIG. 3 shows the third stage of production in which the dry ingredients are added to container 1. The two dry ingredients are sea salt 11 and Epsom salt 12. For our exemplary half gallon batch, two cups of sea salt 11 and one cup of Epsom salt 12 are added to container 1. These two salts are folded into the ingredients of stages one and two and mixed thoroughly. After the above eleven ingredients of have been combined in container 1 the present skin conditioner is basically complete and ready for packaging or for use. Optionally, one or more essential oils can be added at the end of stage three to provide a pleasant fragrance to the conditioner. Some essential oils that may be added include citrus limon, citrus reticulatea berginia, odorata, rose geranium, lavender and sage. The essential oils are for aesthetic purposes only. The conditioner will perform as intended without the addition of essential oils.

In regards to packaging and shipment, the present conditioner must be packaged and shipped in such a way that controls seepage, pressure and temperature. The molecular structure of some of the ingredients may change if the conditioner is heated to temperatures above 100° F. Further, molecular structures may change if the conditioner experiences variations in air pressure. Therefore, shipment of the conditioner should be made by ground or sea and not by air.

Figure 4:
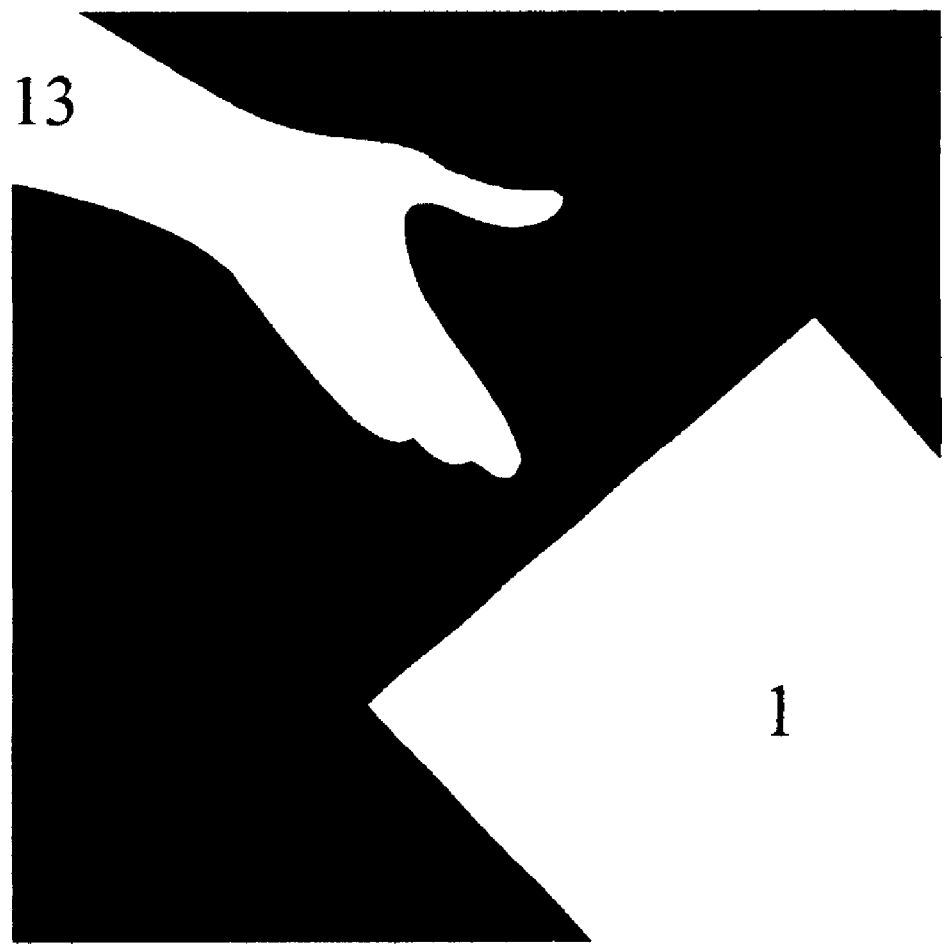
FIG. 4 illustrates a method for applying the present conditioner.

FIG. 4 shows a hand 13 of a user being used to scoop up a desired amount of the present conditioner out of container 1 for application to the skin. Prior to application the conditioner should be mixed so that any of the salts that have settled on the bottom of container 1 are uniformly dispersed throughout the conditioner. Optionally, container 1 can be placed in hot water to heat the conditioner prior to application. Heating of the conditioner should not exceed a temperature of 100° F. for the same reasons mentioned above, because it may cause a change in the molecular structure of some of the ingredients. Both the heated and unheated conditioner will provide the benefits of eliminating body dandruff and conditioning the skin so that the user is left with "skin like an angel". The heating, or warming, of the conditioner simply makes the conditioner feel better when it is being applied to the skin. If the user is relaxed and soothed by the application of the warmed conditioner than additional therapeutic value is gained. Although hand application is shown in FIG. 4, the present conditioner may also be applied with a flat stick, a cloth or other applicator.

Figure 5:
FIG. 5 indicates the areas of the body that are appropriate for application of the present conditioner.

FIG. 5 is intended to illustrate that the present conditioner is beneficial to both men 14 and women 15. And more importantly, that the conditioner can be applied from head to toe providing benefits to the entire body including the hair and scalp. During application, the conditioner is massaged into the skin and thereafter washed or showered off of the skin. There is no maximum time limit as to how long the conditioner can be left on the skin. If the conditioner is applied to the scalp, the user's hair should be shampooed after application.

In the spirit of full disclosure the following cautions are provided. The present conditioner may lighten color treated hair. If applied to freshly shaved or waxed skin the conditioner will sting. The conditioner will also sting if it gets in the users eyes or open wounds. If the conditioner is eaten it will cause diarrhea. Finally, the present conditioner is slippery and caution should be used especially when getting into and out of the tub or shower. Any conditioner that gets on surfaces other than the skin should be cleaned up to avoid future accidents.

The foregoing description of the specific embodiments will so fully reveal the general nature of the invention that others can, by applying current knowledge, readily modify and/or adapt for various applications such specific embodiments without departing from the generic concept. Therefore, such adaptations and modifications should and are intended to be comprehended within the meaning and range of equivalents of the disclosed embodiments. It is to be understood that the phraseology of terminology employed herein is for the purpose of description and not of limitation.

We claim:

1. A skin conditioner that eliminates body dandruff, cleanses a skin of a user and leaves the user with soft and supple skin, wherein the conditioner is stirred prior to application so that a generally uniform consistency is obtained, and the conditioner is washed or showered off sometime after application, the skin conditioner consisting of:
   sea salt;
   Epsom salt and aloe vera gel, wherein an amount of Epsom salt and aloe vera gel each is half an amount of the sea salt;
   a first group of ingredients consisting of equal amounts of cold expeller pressed oils of:
      almond;
      apricot kernel;
      avocado; and,
      jojoba;
   and, a second group of ingredients consisting of:
      castor oil;
      vitamin E;
      vegetable glycerin; and,
      soap;
   wherein amounts of the second group of ingredients is substantially less than the amounts of the first group of ingredients, and;
   a result of combining the salts, the gel, the first group of ingredients and the second group ingredients being that the conditioner is able to exfoliate, cleanse and condition all of the skin on the user, including a scalp.

2. The skin conditioner of claim 1, wherein the conditioner is heated, not above 100° F., prior to application to the skin.

3. The skin conditioner of claim 1, wherein the amount of sea salt is 2 cups, the amounts of Epsom salt and aloe vera gel are 1 cup, the approximately equal amounts of each of the first group of ingredients is approximately 1 cup, and the amounts of each of the second group of ingredients is equal to or less than 1 tablespoon.

4. The skin conditioner of claim 1, wherein an applicator or a hand is used to apply the conditioner to the skin of the user's entire body so that body dandruff is eliminated from the entire body and the skin of the entire body is conditioned.

5. The conditioner of claim 1, wherein the conditioner is applied to the scalp of the user to eliminate dandruff and condition the scalp and hair.

6. The conditioner of claim 3, wherein the amounts of all of the ingredients are proportionately increased to produce larger batches of the conditioner.

7. A method of using a skin conditioner proportionately consisting of: 2 cups of sea salt; approximately 1 cup each of Epsom salt, almond oil, apricot kernel oil, avocado oil, jojoba oil, and aloe vera gel; and approximately 1 tablespoon each of castor oil, vitamin E, vegetable glycerin soap; and an essential oil, the method comprising the steps of:

stirring the skin conditioner so that a generally uniform consistency is obtained;

using an applicator or a hand to apply the conditioner to part of a body or the entire body;

massaging the conditioner into skin of the body; and, showering or otherwise rinsing residual conditioner and dead skin cells off of the skin, a result being that the conditioner exfoliates, cleanses and conditions the skin of the body, including a scalp.

8. The method of claim 7, further comprising the step of:

heating the conditioner, not above 100° F., prior to applying the conditioner to the skin.

9. The method of claim 7, wherein the step of massaging further comprises the step of:

leaving the skin conditioner on the skin for a period of time before rinsing or showering off the conditioner.

10. The method of claim 7, wherein the step of massaging further comprises massaging the conditioner into the scalp to eliminate dandruff and to condition hair.

11. A method of making a skin conditioner wherein the conditioner consists of: sea salt; Epsom salt; almond oil; apricot kernel oil; avocado oil; jojoba oil; aloe vera gel; castor oil; vitamin E; vegetable glycerin, soap; and an essential oil, the method comprising the steps of:

combining in a container essential oil, 1 cup of aloe vera gel, 1 tablespoon each of castor oil, vegetable glycerin and soap, with 1 teaspoon of vitamin E;

beating the combined aloe vera gel, castor oil, vegetable glycerin, soap, an essential oil and vitamin E until they are well blended;

adding to the container ¾ of a cup each of almond oil, apricot kernel oil, avocado oil and jojoba oil;

mixing contents of the container well; and, folding in to the contents of the container 2 cups of sea salt and 1 cup of Epsom salt;

a result being that the conditioner is able to exfoliate, cleanse and condition all skin of a user, including a scalp.

12. The method of claim 11, further comprising the step of:

heating the contents of the container, not above 100° F., prior to use of the conditioner.

13. The method of claim 11, wherein amounts of each of ingredient are proportionately increased to make larger batches of the skin conditioner.

14. The method of claim 11, wherein the conditioner is used on all or part of the user's skin including the scalp and hair.

* * * * *